US011666261B2

(12) United States Patent
Kawabata et al.

(10) Patent No.: US 11,666,261 B2
(45) Date of Patent: Jun. 6, 2023

(54) BIOMAGNETISM MEASUREMENT DEVICE

(71) Applicants: National University Corporation Tokyo Medical and Dental University, Tokyo (JP); TDK CORPORATION, Tokyo (JP)

(72) Inventors: Shigenori Kawabata, Tokyo (JP); Tomohiko Shibuya, Tokyo (JP)

(73) Assignees: National University Corporation Tokyo Medical and Dental University, Tokyo (JP); TDK CORPORATION, Tokyo (JP)

( * ) Notice: Subject to any disclaimer, the term of this patent is extended or adjusted under 35 U.S.C. 154(b) by 449 days.

(21) Appl. No.: 16/756,079

(22) PCT Filed: Aug. 21, 2018

(86) PCT No.: PCT/JP2018/030748
§ 371 (c)(1),
(2) Date: Apr. 14, 2020

(87) PCT Pub. No.: WO2019/077865
PCT Pub. Date: Apr. 25, 2019

(65) Prior Publication Data
US 2020/0237243 A1    Jul. 30, 2020

(30) Foreign Application Priority Data
Oct. 16, 2017    (JP) .............................. JP2017-200389

(51) Int. Cl.
*A61B 5/242*    (2021.01)
*G01R 33/035*   (2006.01)

(52) U.S. Cl.
CPC .......... *A61B 5/242* (2021.01); *G01R 33/0354* (2013.01)

(58) Field of Classification Search
CPC ..................................................... A61B 5/242
See application file for complete search history.

(56) References Cited

U.S. PATENT DOCUMENTS

2007/0120563 A1    5/2007   Kawabata et al.
2013/0150702 A1    6/2013   Hokari
(Continued)

FOREIGN PATENT DOCUMENTS

JP    H01129179 A    5/1989
JP    H0542120 A     2/1993
(Continued)

OTHER PUBLICATIONS

Office Action issued in Japanese Application No. 2019-549132; dated Apr. 13, 2021 (3 pages).
(Continued)

*Primary Examiner* — Rochelle D Turchen
(74) *Attorney, Agent, or Firm* — Osha Bergman Watanabe & Burton LLP

(57) ABSTRACT

An objective of the present invention is to provide a biomagnetism measurement device capable of three-dimensionally acquiring magnetism information of a living body with ease. This biomagnetism measurement device (101) is for measuring biomagnetism using a plurality of magnetic sensors (1) at the same time. The plurality of magnetic sensors (1) is retained by a retaining part (10) (a first retaining portion [11] and a second retaining portion [12]) so as to have different measurement directions. Furthermore, the retaining part (10) (the first retaining portion [11] and the second retaining portion [12]) has arranged thereon the plurality of magnetic sensors (1) so as to enable biomagnetism to be measured at a plurality of sites at the same time.
(Continued)

The magnetic sensor (1) comprises a means for detecting the biomagnetism in a temperature environment commensurate with normal temperature.

10 Claims, 15 Drawing Sheets

(56) References Cited

U.S. PATENT DOCUMENTS

| | | | | |
|---|---|---|---|---|
| 2017/0209062 | A1* | 7/2017 | Iwasaki | .................. H01L 43/10 |
| 2018/0242865 | A1 | 8/2018 | Yamagata | |

FOREIGN PATENT DOCUMENTS

| | | | |
|---|---|---|---|
| JP | 2000175874 | * | 12/1998 |
| JP | 2000-041965 A | | 2/2000 |
| JP | 2007-167616 A | | 7/2007 |
| JP | 201295939 A | | 5/2012 |
| JP | 2013124873 A | | 6/2013 |
| JP | 2017051600 A | | 3/2017 |
| WO | WO-2004017102 A2 * | 2/2004 | ............ B82Y 35/00 |
| WO | 2017/209273 A1 | | 12/2017 |
| WO | 2018/025829 A1 | | 2/2018 |

OTHER PUBLICATIONS

International Search Report issued in Application No. PCT/JP2018/030748 dated Nov. 13, 2018 (5 pages).

Written Opinion issued in International Application No. PCT/JP2018/030748 dated Nov. 13, 2018 (5 pages).

"Success in measurement of heart activity by the MR sensors" TDK, Internet(https://eetimes.jp/eelarticles/1606/09/news029.html ), Japan, Jun. 9, 2016 (2 pages).

Office Action issued in Japanese Application No. 2019-549132; dated Jan. 6, 2021 (6 pages).

Supplementary European Search Report in counterpart European Application No. 18867849.4 dated Oct. 8, 2020 (7 pages).

* cited by examiner

FIG. 12A
FIG. 12B
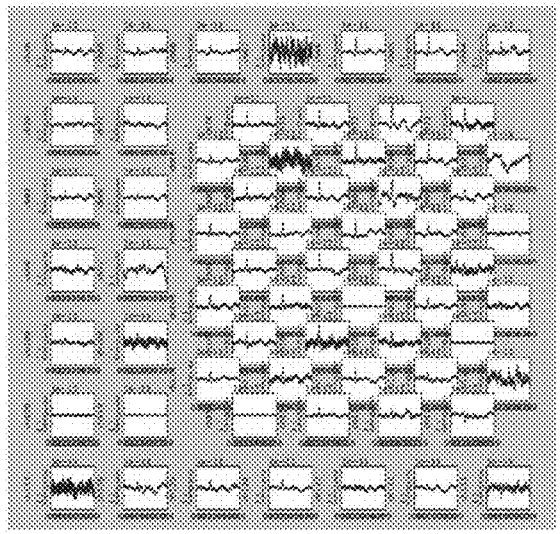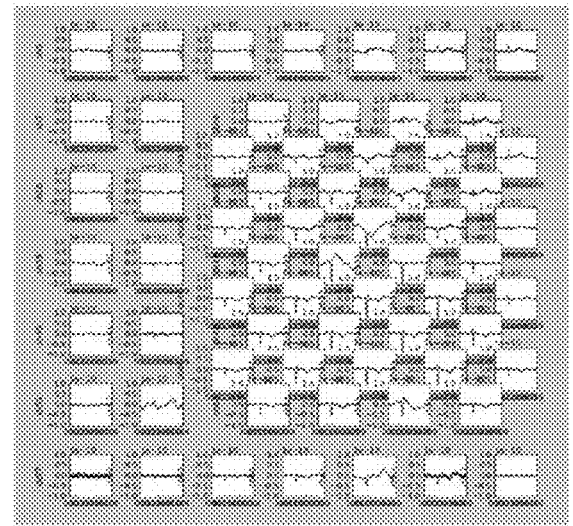
FIG. 13
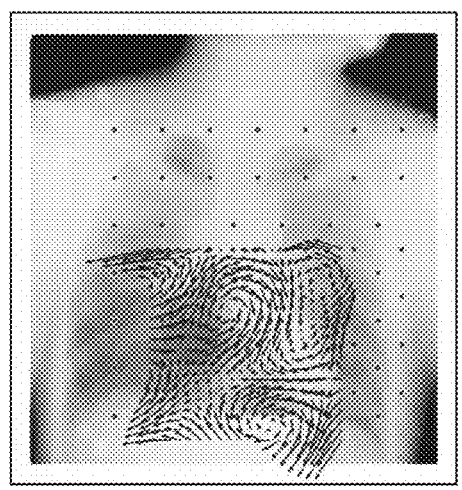

BIOMAGNETISM MEASUREMENT DEVICE

TECHNICAL FIELD

The present invention relates to a biomagnetism measuring device with a magnetic sensor.

BACKGROUND ART

Recently, biomagnetism measuring devices such as a magnetoencephalograph, a magnetocardiograph and a magnetomyograph have been used in medical settings, that detect weak magnetism (magnetic field) of low frequency generated in accordance with electrical activities of the brain, the heart, and muscles of a living organism. Strength of cerebral magnetism that accompanies the electrical activities of the brain is about one hundred-millionth of the strength of the earth's magnetism, and the strength of cardiomagnetism that accompanies the electrical activities of the cardiac muscle is about one millionth of the strength or the earth's magnetism. Therefore, upon detection of magnetism generated by the living organism (hereinafter, may be also referred to as "biomagnetism"), extremely high sensitivity is required as detection performance of a magnetic sensor.

As a high-sensitivity magnetic sensor that enables highly sensitive magnetism detection, a superconducting quantum interference device (hereinafter, may be also referred to as "SQUID") has been known (for example, see Patent Document 1).

On the other hand, the use of an MR sensor width a magnetic resistance element (MR element) is also considered, that is capable of detecting weak magnetism in a normal temperature range with no need for cooling. Since the MR sensor does not need to be placed in a cooling vessel (Dewar vessel), a biomagnetism measuring device with the MR sensor has advantages of lower cost, ease of handling, and ease or bringing the sensor close to the living organism, compared to the case of using the SQUID sensor.

Patent Document 1: Japanese Unexamined Patent Application, Publication No. 2000-41965

DISCLOSURE OF THE INVENTION

Problems to be Solved by the Invention

However, regardless of whether the SQUID sensor or the MR sensor is used, the conventional biomagnetism measuring devices have typically detected magnetism only in a tangential component substantially parallel to the body surface of the living organism. More specifically, the magnetic sensor has typically been arranged two-dimensionally on a plane substantially parallel to the body surface of the living organism. As a result, two-dimensional biomagnetic information with respect to the body surface of the living organism could be obtained, while three-dimensional biomagnetic information including a biomagnetic component in a depth direction with respect to the body surface of the living organism could not be obtained. In this regard, obtaining of more detailed biomagnetic information is awaited.

It is to be noted that Patent Document 1 proposes a biomagnetism measuring apparatus in which a cooling vessel including a SQUID sensor is configured in a substantially L-shape such that the SQUID sensor is located as close as possible to an anterior part and a posterior part or a subject's body. However, it is technically difficult to arrange the SQUID sensor in the substantially L-shaped cooling vessel, and it is also difficult to arrange the SQUID sensor at the optimal position for the subject of the measurement. Furthermore, it is difficult to carry out the measurement in an upright position and a seated position, in addition to a supine position and a prone position; and to adjust the position in accordance with the physical constitution of the subject.

An object of the present invention is to provide a biomagnetism measuring device that is capable of obtaining biomagnetic information three-dimensionally in a convenient manner.

Means for Solving the Problems

The present inventors have found that biomagnetic information can be obtained three-dimensionally in a convenient manner by employing magnetic sensors that detect biomagnetism in a thermal environment commensurate with normal temperature, the magnetic sensors being arranged at such positions that a plurality of components of the biomagnetism can be detected simultaneously, and thus accomplished the present invention.

(1) According to the present invention, in a biomagnetism measuring device for measuring biomagnetism simultaneously with a plurality of magnetic sensors: the plurality of magnetic sensors is held by a holder portion so as to have different measuring directions; the plurality of magnetic sensors provided at the holder portion so as to be capable of measuring biomagnetism of multiple sites simultaneously; and the plurality of magnetic sensors comprises a sensor that detects the biomagnetism in a thermal environment commensurate with normal temperature.

(2) According to the present invention, in the biomagnetism measuring device according to (1), the holder portion provided with a first holder portion in which the plurality of magnetic sensors is arranged two-dimensionally at positions in a (x-y) coordinate substantially parallel to a body surface of a living organism, and a second holder portion in which the plurality of magnetic sensors is arranged two-dimensionally at positions in a coordinate different from the (x-y) coordinate.

(3) According to the present invention, in the biomagnetism measuring device according to (2), first holder face of the first holder portion on which the plurality of magnetic sensors is arranged and a second holder face of the second holder portion on which the plurality of magnetic sensors is arranged are arranged at a substantially right angle in a cross-sectional view.

(4) According to the present invention, in the biomagnetism measuring device according to (2) or (3), the holder portion is provided with: a third holder portion in which the plurality of magnetic sensors is arranged two-dimensionally; an opening/closing mechanism that enables the third holder portion to open and close with respect to the first holder portion or the second holder portion; and a moving mechanism that enables the third holder portion to move toward the first holder portion or the second holder portion.

(5) According to the present invention, in the biomagnetism measuring device according to any one of (1) to (4), the plurality of magnetic sensors comprises a SQUID sensor.

(6) According to the present invention, in the biomagnetism measuring device according to any one of (1) to (5), a plurality of holding frames that holds the plurality of magnetic sensors removably or movably is arranged in an array in the holder portion.

(7) According to the present invention, in the biomagnetism measuring device according to any one of (1) to (6), a plurality of rails that slidably holds the plurality of magnetic sensors is arranged in the holder portion.

(8) According to the present invention, in the biomagnetism measuring device according to any one of (1) to (7), the holder portion provided with the moving mechanism that moves the plurality of magnetic sensors individually in a contact/separation direction with respect to the living organism.

(9) According to the present invention, in the biomagnetism measuring device according to any one of (1) to (8), the holder portion is composed of a non-magnetic material.

(10) According to the present invention, in the biomagnetism measuring device according to any one of (1) to (9), the holder portion composed of a flexible material.

Effects of the Invention

The present invention can provide a biomagnetism measuring device that is capable of obtaining biomagnetic information three-dimensionally in a convenient manner. In addition, the present invention can obtain the three-dimensional biomagnetic information which can be overlaid on three-dimensional images generated by diagnostic imaging devices such as a magnetic resonance imaging (MRI) device and an X-ray computed tomography (CT) device, and is therefore useful in diagnosis of heart diseases and neurological diseases.

Furthermore, in the present invention, the magnetic sensor that detects the biomagnetism in a thermal environment commensurate with normal temperature can be easily moved. As a result, unlike the case of using only the SQUID sensor which needs to be fixed, the magnetic sensor can be arranged at the optimal position for the subject of the measurement.

BRIEF DESCRIPTION OF THE DRAWINGS

FIG. 12(a) is a diagram showing magnetic field waveform data obtained by the magnetic sensor in a first holder portion arranged on an anterior side of a subject;

FIG. 12(b) is a diagram showing magnetic field waveform data obtained by the magnetic sensor 1 in a second holder portion arranged on a lateral side of a subject;

FIG. 13 is a diagram showing an example of biological information in which magnetocardiogram data built from biological signal data obtained from the biomagnetism measuring device is overlaid on an X-ray (CT) image;

PREFERRED MODE FOR CARRYING OUT THE INVENTION

Embodiments of the present invention are described in detail hereinafter; however, the present invention is not limited to the embodiments and can be embodied with appropriate modifications.

The biomagnetism measuring device according to the present embodiment is for measuring biomagnetism simultaneously with a plurality of magnetic sensors, in which the plurality of magnetic sensors is held by a holder portion so as to have different measuring directions and detects biomagnetism of a plurality of directional components for biomagnetism of one site. Furthermore, a plurality of magnetic sensors provided at the holder portion so as to be capable of simultaneously measuring biomagnetism of multiple sites according to a desired measurement range, and detects biomagnetism of a plurality of directional components for biomagnetism of each of the multiple sites. Here, the "biomagnetism of one site" means biomagnetism generated in a site detectable by one magnetic sensor, and the biomagnetism in the site may be generated from one or a plurality of sources.

For example, as described later, the magnetic sensor arranged at a predetermined coordinate position (x, y) in a (x-y) coordinate substantially parallel to the body surface of the living organism detects an x-direction component or a y-direction component of the biomagnetism in one site, while the magnetic sensor arranged at a predetermined coordinate position (y, z) in a (y-z) coordinate detects a z-direction component of the biomagnetism in one site. Furthermore, by arranging a plurality of magnetic sensors two-dimensionally respectively at a plurality of coordinate positions in the (x-y) coordinate and the (y-z) coordinate in order to detect biomagnetism of multiple sites simultaneously, three-dimensional biomagnetic information including components of three or more directions can be obtained.

Since the biomagnetism measuring device according to the present embodiment detects a plurality of directional components for biomagnetism of one site by means of the plurality of magnetic sensors, more detailed biomagnetism information can be obtained compared to the case of measuring only a unidirectional component of biomagnetism of one site by means of one magnetic sensor.

Hereinafter, specific embodiments of the present invention are described with reference to the drawings. It is to be noted that the drawings may present enlarged views of components for the sake of expediency, in order to emphasize characteristic features of the present invention, and therefore the number, dimension proportion and the like of each constitutive element may be different from actual ones.

Biomagnetism Measuring Device According to First Embodiment

Figure 1:
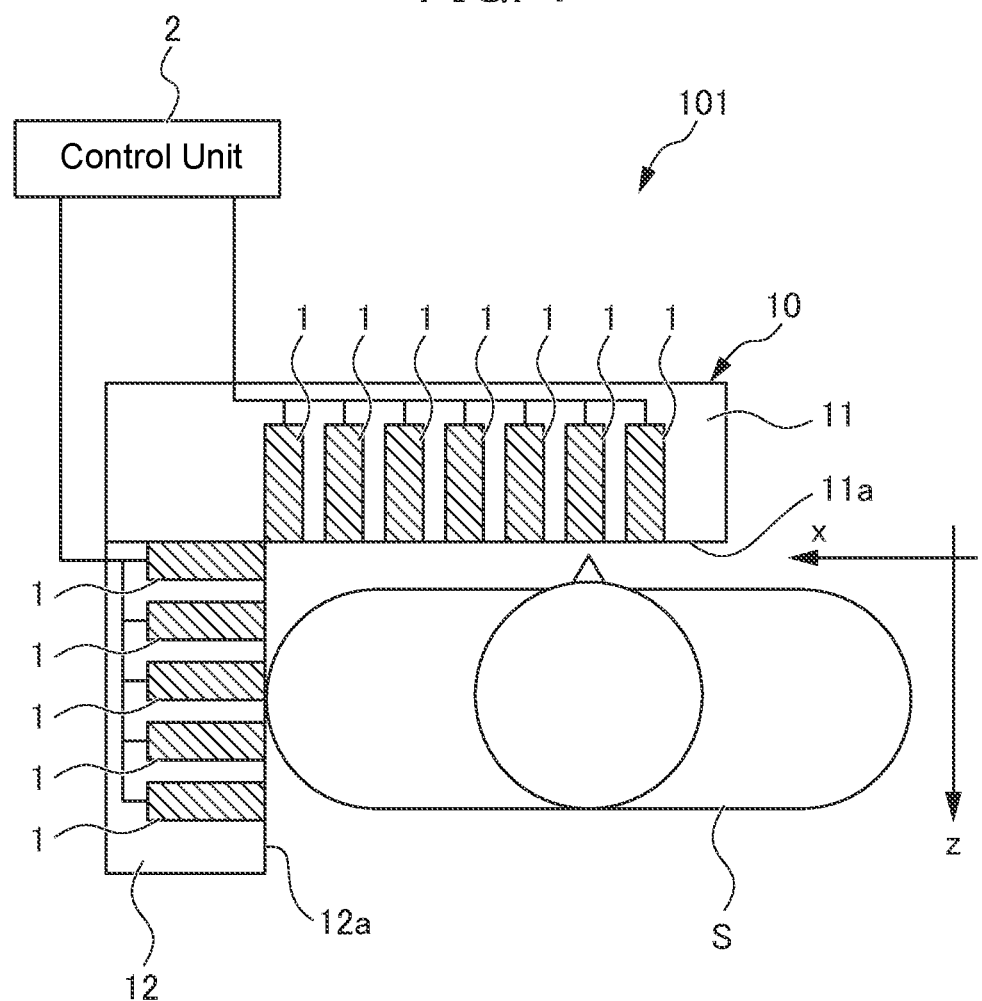
FIG. 1 is a schematic cross-sectional schematically showing a configuration a biomagnetism measuring device according to a first embodiment.
Figure 2:
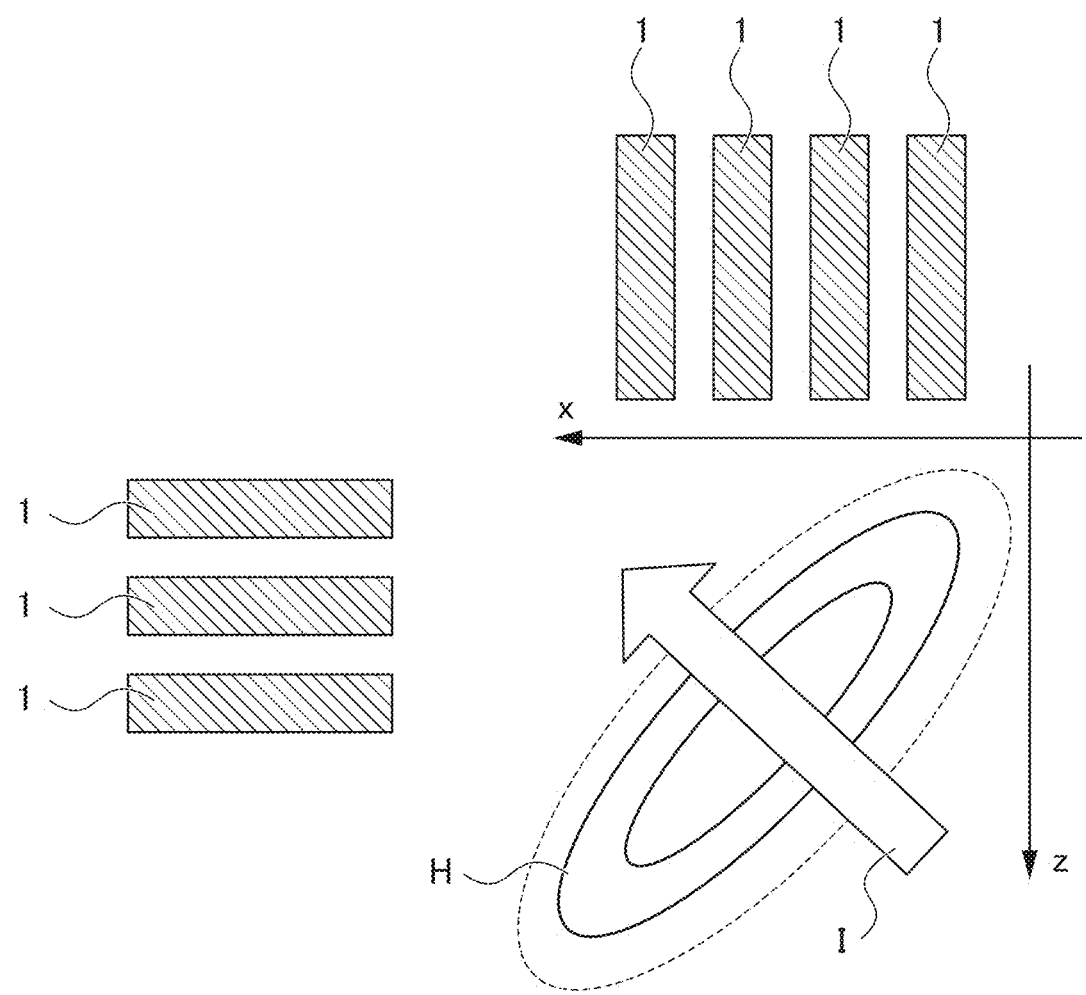
FIG. 2 is a schematic view showing a positional relationship between a magnetic sensor and biomagnetism.

FIG. 1 is a schematic cross-sectional view schematically showing a configuration of the biomagnetism measuring device according to the first embodiment. FIG. 2 is a schematic view showing a positional relationship between the magnetic sensor and biomagnetism. As shown in FIG. 1, in a biomagnetism measuring device 101 according to the first embodiment, a plurality of magnetic sensors 1 is held by a holder portion 10, the holder portion 10 being formed in a substantially L-shape in a cross-sectional view and arranged so as to surround a left side of the body of a subject S as the living organism. As shown in FIG. 2, the biomagnetism measuring device 101 detects, by means of the plurality of magnetic sensors 1, weak biomagnetic field (biomagnetism) H from bioelectric current I in the subject S (for example, heart) generated by electrical stimulation from a stimulation apparatus.

Magnetic Sensor

The magnetic sensor 1 may be an arbitrary magnetic sensor which can detect magnetism of about $10^{-4}$ T (Tesla) to $10^{-10}$ T, in at least one axial direction in a thermal environment commensurate with normal temperature.

Preferred examples of the magnetic sensor 1 include a giant magnetoresistive (GMR) sensor, a tunnel magnetoresistive (TMR) sensor, an anisotropic magnetoresistive (AMR) sensor, a magnetic impedance (MI) sensor, a fluxgate sensor, an optically pumped magnetic sensor, and the like.

The magnetic sensors 1 exemplified above are preferred for the following reasons: being capable of obtaining similar amount of information to the SQUID sensor; needing no temperature control mechanism such as a cooling vessel containing a cooling medium, e.g., liquid helium, liquid nitrogen, etc. unlike the SQUID sensor; being easy to handle (displacement, exchange, removal, etc.); and being easy to be brought close to the living organism.

It is to be noted that the "thermal environment commensurate with normal temperature" as used in the present invention means an environment (room temperature) in which a temperature control mechanism not necessary for controlling the temperature of the magnetic sensor or an environment in which only a temperature control mechanism that can be conveniently used such as a thermal insulating material is required for cooling or heating, for example −10° C. to 250° C.

Holder Portion

The holder portion 10 is composed of a first holder portion 11 arranged on an anterior side (in front of chest) of the subject S, and a second holder portion 12 arranged on a lateral side of the subject S. In the first holder portion 11, the plurality of magnetic sensors 1 that detects magnetism of an x component or a y component (hereinafter, may be also referred to as "tangential component") substantially parallel to the body surface of the subject S is arranged two-dimensionally in array at coordinate positions in the (x-y) coordinate. As a result, two-dimensional biomagnetic information of the (x-y) coordinate can be obtained from the plurality of magnetic sensors 1 held by the first holder portion 11.

In the second holder portion 12, the plurality of magnetic sensors 1 that detects magnetism of a z component (hereinafter, may be also referred to as "normal component") substantially perpendicular to the body surface of the subject S is arranged two-dimensionally in array at coordinate positions in the (y-z) coordinate. As a result, two-dimensional biomagnetic information of the (y-z) coordinate can be obtained from the plurality of magnetic sensors 1 held by the second holder portion 12. Here, a first holder face 11a of the first holder portion 11 on which detection faces of the plurality of magnetic sensors 1 are exposed and a second holder face 12a of the second holder portion 12 on which detection faces of the plurality of magnetic sensors 1 are exposed intersect with each other at a substantially right angle in a cross-sectional view (L-shape in the first embodiment).

Control Unit

A control unit 2 is provided with: an A/D conversion means that carries out A/D conversion of the biomagnetic information (biological signal) which is output from the plurality of magnetic sensors 1 held by the first holder portion 11 and the second holder portion 12 according to a preset sampling frequency, to obtain biological signal data; a recording means that records a plurality of pieces of biological signal data (magnetic field waveform data) obtained by the A/D conversion according to the sampling frequency; a processing means that processes, by a predetermined computing method, the plurality of pieces of biological signal data recorded in the recording means within a predetermined period, to eventually obtain three-dimensional biomagnetic information; an output means that outputs to an external display device the biomagnetic information being processed or having been processed by the processing means; and the like.

It is to be noted that the computing method employed by the processing means is not particularly limited, and may be exemplified by addition averaging, moving averaging, wiener filtering, low-pass filtering (LPF) , high-pass filtering (HPF), band-pass filtering (BPF), band-elimination filtering (BEF) and the like. Among these, in light of reduction of noise such as environmental magnetism, addition averaging of the plurality of pieces of magnetic field waveform data for generating addition averaged waveform data is preferred as the computing method.

As described above, a biomagnetism measuring device in which the magnetic sensor 1 is held only in the first holder portion 11 can only obtain two-dimensional biomagnetic information, while the biomagnetism measuring device 101 in which the magnetic sensor 1 is held in both the first holder portion 11 and the second holder portion 12 can obtain three-dimensional biomagnetic information. The three-dimensional biomagnetic information obtained by the biomagnetism measuring device 101 can be overlaid on three-dimensional images obtained by a magnetic resonance imaging (MRI) device or an X-ray computed tomography (CT) device, and is therefore useful in diagnosis of heart diseases and neurological diseases.

Biomagnetism Measuring Device According to Second Embodiment

The biomagnetism measuring device 102 according to the second embodiment is different from the biomagnetism measuring device 101 according to the first embodiment in that the magnetic sensor 1 is provided, in addition to the anterior side and the lateral side of the subject S, in a region between the anterior side and the lateral side as described later.

Figure 3:
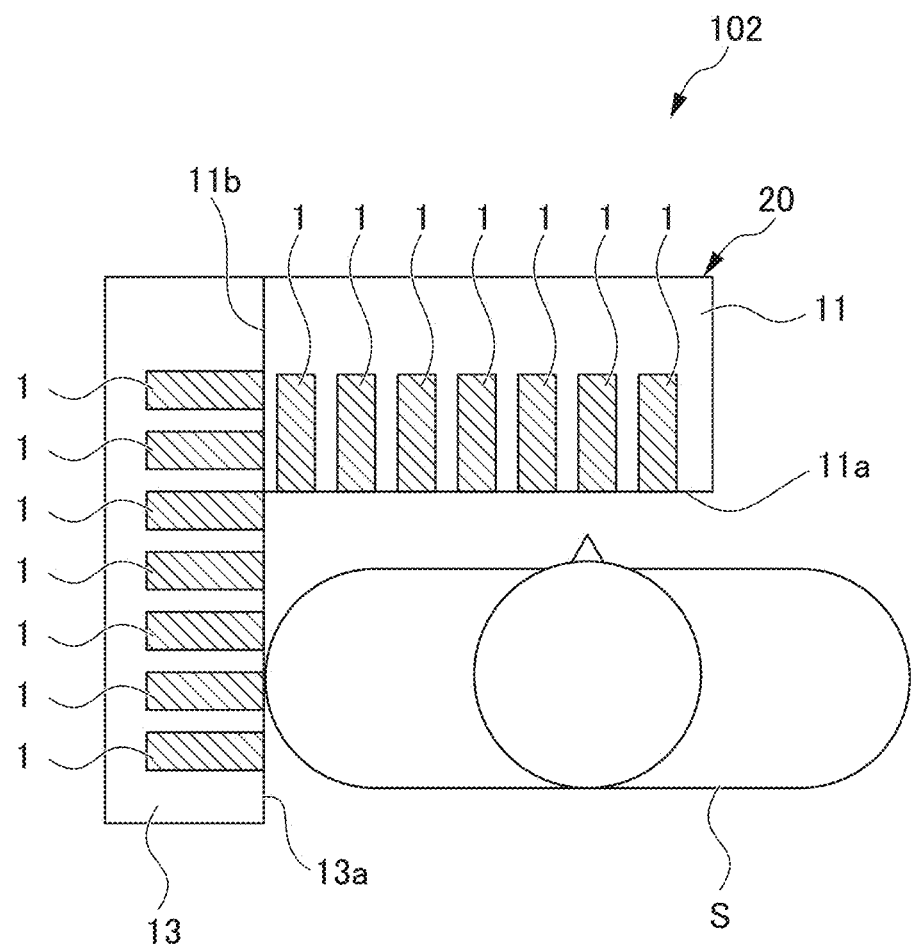
FIG. 3 is a schematic cross-sectional view schematically showing a configuration example of a biomagnetism measuring device according to a second embodiment.

FIG. 3 is a schematic cross-sectional view schematically showing a configuration example of a biomagnetism measuring device according to the second embodiment. Hereinafter, members identical to those described above are referred to with the same reference symbols and explanation thereof may be omitted. As shown in FIG. 3, in the biomagnetism measuring device 102 according to the second embodiment, a plurality of magnetic sensors 1 is held by a holder portion 20. The holder portion 20 is composed of a first holder portion 11 arranged on an anterior side of the subject S, and a second holder portion 13 arranged on a lateral side of the subject S and a lateral face 11b side of the first holder portion 11.

In the first holder portion 11, the plurality of magnetic sensors 1 that detects magnetism of a tangential component of the subject S is arranged two-dimensionally in array at coordinate positions in the (x-y) coordinate. As a result, two-dimensional biomagnetic information of the (x-y) coordinate can be obtained from the plurality of magnetic sensors 1 held by the first holder portion 11.

In the second holder portion 13, the plural of magnetic sensors that detects magnetism of a normal component of the S is arranged two-dimensionally in array at coordinate positions in the (y-z) coordinate. As a result, two-dimensional biomagnetic information of the (y-z) coordinate can be obtained from the plurality of magnetic sensors 1 held by the second holder portion 13. Here, a first holden face 11a of the first holder portion 11 on which detection faces of the plurality of magnetic sensors 1 are exposed and a second holder face 13a of the second holder portion 13 on which detection faces of the plurality of magnetic sensors 1 are exposed intersect with each other at a substantially right angle in a cross-sectional view (T-shape in the second embodiment).

In the biomagnetism measuring device 101 according to the first embodiment, the magnetic sensor 1 is not provided in a region between the anterior side and the lateral side of the subject S (region on the lateral face 11b side of the first holder portion 11 in the second embodiment). Therefore, biomagnetism outside of a detection scope of the magnetic sensor 1 in the first holder portion 11 closest to the second holder portion 12, and a detection scope of the magnetic sensor 1 in the second holder portion closest to the first holder portion 11 cannot be detected.

In this regard, in the biomagnetism measuring device 102 according to the second embodiment, the first holder face 11a and the second holder face 13a intersect with each other in a substantially T-shape in a cross-sectional view, and the magnetic sensor 1 is provided also in the region between the anterior side and the lateral side of the subject S (region facing the lateral face 11b), as described above. As a result, the biomagnetism measuring device 102 according to the second embodiment is capable of detecting the biomagnetism outside of the detection scopes described above.

For example, when the biomagnetic field H is reversed outside or these detection scopes, the reversal can be detected. As described above, the first holder face 11a and the second holder face 13a intersecting with each other in a substantially T-shape on one side of the biomagnetism measuring device 102 is particularly useful for detecting biomagnetism of the heart of the subject S which is slightly on the left side of the center of its body.

Biomagnetism Measuring Device According to Third Embodiment

The biomagnetism measuring device 103 according to the third embodiment is different from the biomagnetism measuring device 102 according to the second embodiment in that the magnetic sensor 1 is also provided on the dorsal side of the subject S as described later.

Figure 4:
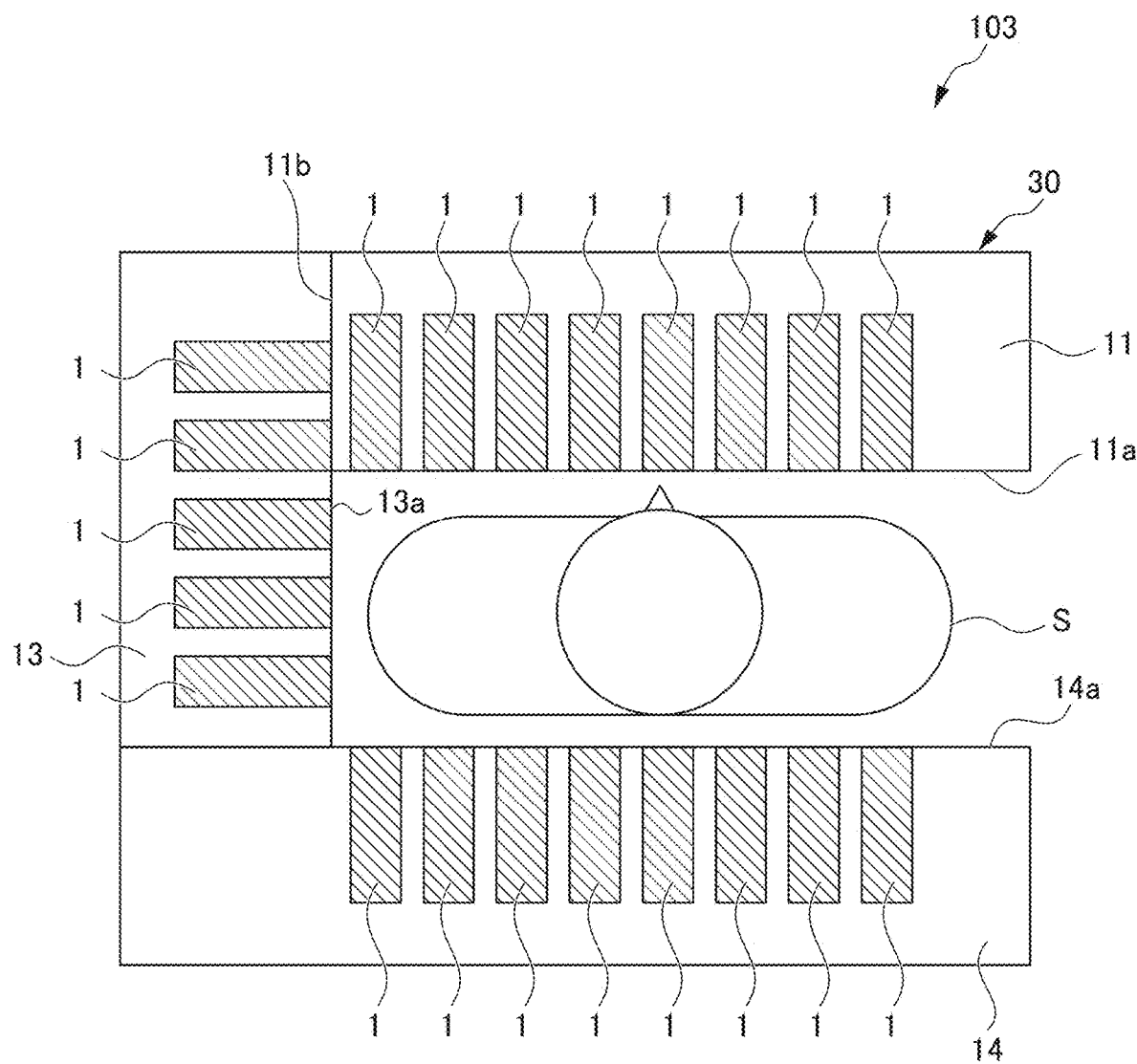
FIG. 4 is a schematic cross-sectional view schematically showing a configuration example of a biomagnetism measuring device according to a third embodiment.

FIG. 4 is a schematic cross-sectional view schematically showing a configuration example of a biomagnetism measuring device according to a third embodiment. As shown FIG. 4, in the biomagnetism measuring device 103 according to the third embodiment, a plurality of magnetic sensors 1 is held by a holder portion 30. The holder portion 30 is composed of a first holder portion 11 arranged on an anterior side of the subject S, a second holder portion 13 arranged on a left side of the subject S and a lateral face 11b side of the first holder portion 11, and a third holder portion 14 arranged on the dorsal side or the subject S.

In the first holder portion 11 and the third holder portion 14, the plurality of magnetic sensors that detects magnetism of a tangential component of the subject S is arranged two-dimensionally in array at coordinate positions in the (x-y) coordinate. As a result, two-dimensional biomagnetic information of the (x-y) coordinate of the anterior side and the dorsal side of the subject S can be obtained from the plurality of magnetic sensors held by the first holder portion 11 and the third holder portion 14.

In the second holder portion 13, the plurality of magnetic sensors that detects magnetism of a normal component of the subject S is arranged two-dimensionally in array at coordinate positions in the (y-z) coordinate. As a result, two-dimensional biomagnetic information of the (y-z) coordinate can be obtained from the plurality of magnetic sensors 1 held by the second holder portion 13. Here, a first holder face 11a of the first holder portion 11 on which detection faces of the plurality of magnetic sensors 1 are exposed and a second holder face 13a of the second holder portion 13 on which detection faces of the plurality of magnetic sensors 1 are exposed intersect with each other in a substantially T-shape in a cross-sectional view.

As described above, the biomagnetism measuring device 103 according to the third embodiment is capable of obtaining the more detailed biomagnetism information than the biomagnetism measuring devices 101, 102 according to the first and second embodiments, since the magnetic sensors 1 held by the first holder portion 11, the third holder portion 14, and the second holder portion 13 can detect biomagnetism of the anterior side, the dorsal side, the left side, and the region between the anterior side and the lateral side of the subject S. Alternatively, a configuration of surrounding the subject S may be employed in which a fourth holder portion is provided on the right side of the subject S to arrange the magnetic sensors 1 on both sides of the subject S.

Here, the first holder portion 11, the third holder portion 14, and the second holder portion 13 may have a mechanism of moving horizontally or vertically to get closer to the subject S. Furthermore, in order to facilitate introduction of the subject S into a measurement area, an open/close mechanism or a separation mechanism is preferably provided between the first holder portion 11 or the second holder portion 13 and the third holder portion 14.

For example, an open/close mechanism can be provided by connecting the second holder portion 13 and the third holder portion 14 with an arm, in which the subject S can be easily introduced into the measurement area by opening the third holder portion 14. And then, by detecting the biomagnetism with the third holder portion 14 being closed, the biomagnetism of the dorsal side of the subject S which is difficult to detect only by the magnetic sensors 1 in the first holder portion 11 can be easily detected by the magnetic sensor 1 in the third holder portion 14. Furthermore, by providing a moving mechanism that makes the third holder portion 14 movable toward the first holder portion 11, various physical constitutions (for example, thickness of the chest) of the subject S can be supported.

It is to be noted that, in the biomagnetism measuring devices 102, 103 according to the second and third embodiments, a part of the second holder face 13a, on which detection faces of the plurality of magnetic sensors 1 are exposed, faces the lateral face 11b of the first holder portion 11 in order to detect magnetism of the region between the anterior side and the lateral side of the subject S; however, the present invention is not limited to this configuration.

For example a configuration may be employed in which: a part of the first holder face 11a of the first holder portion 11 extends to face the lateral face of the second holder portion 13 facing the lateral side of the subject S; the magnetic sensor 1 is provided also in the extended part such that the detection face is exposed; and the first holder face 11a (including the extended part) and the second holder face 13a intersect with each other in a substantially T-shape in a cross-sectional view.

It is to be noted that, in the biomagnetism measuring devices 101, 102, 103 according to the first to third embodiments, the first holder face 11a is arranged in the (x-y) coordinate and the second holder faces 12a, 13a are arranged in the (y-z) coordinate on the basis of the (x-y-z) coordinate perpendicular to each other; however, the first holder face 11a and the second holder faces 12a, 13a are not required to be perpendicular to each other as long as positional information of the magnetic sensor 1 can be identified.

Furthermore, in the biomagnetism measuring devices 101, 102, 103 according to the first to third embodiments, the subject S in an upright position during measurement; however, the position of the subject S may be any of an upright position, a seated position, supine position and a prone position. For example, a part of a bed may be configured as the holder portion and the subject S may be in a supine position and a prone position on the bed.

In the case in which the subject S is in a supine position or a prone position on the bed, the body surface of the subject S is in closer contact with the detection face of the magnetic sensor 1, and consequently more accurate biomagnetic information can be obtained. Furthermore, if the holder portions 10, 20, 30 are provided with a rotation mechanism, the magnetic sensor 1 can be positioned at an arbitrary angle, and an upright position, a supine position and a position in between can be supported.

Biomagnetism Measuring Device According to Fourth Embodiment

The biomagnetism measuring device 104 according to the fourth embodiment is different from the biomagnetism measuring device 101 according to the first embodiment in that the SQUID sensor 41 provdded in the holder portion 40 as described later.

Figure 5:
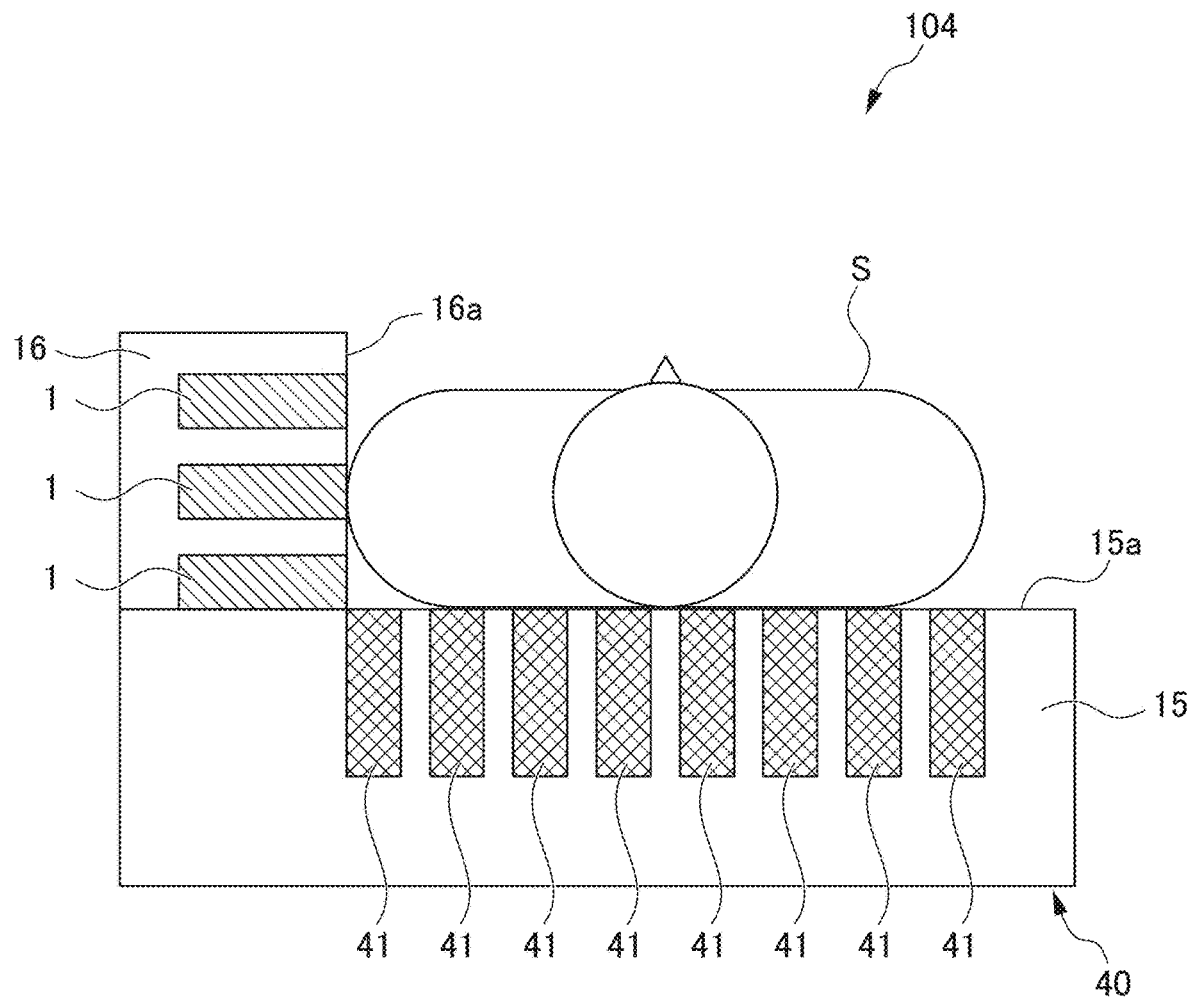
FIG. 5 is a schematic cross-sectional view schematically showing a configuration example of a biomagnetism measuring device according to a fourth embodiment.

FIG. 5 is a schematic cross-sectional view schematically showing a configuration example of a biomagnetism measuring device according to a fourth embodiment. As shown in FIG. 5, the biomagnetism measuring device 104 according to the fourth embodiment includes a holder portion 40 that also serves as a bed. The holder portion 40 is composed of a first holder portion 15 that holds the subject S in a supine position, and a second holder portion 16 arranged on a lateral side of the subject S.

In the first holder portion 15, a plurality of SQUID sensors 41 that detects magnetism of a tangential component of the subject S is arranged two-dimensionally in array at coordinate positions in the (x-y) coordinate. As a result, two-dimensional biomagnetic information of the (x-y) coordinate can be obtained from the plurality of SQUID sensors 41 held by the first holder portion 15.

In the second holder portion 16, the plurality of magnetic sensors that detects magnetism of a normal component or the subject S is arranged two-dimensionally in array at coordinate positions in the (y-z) coordinate. As a result, two-dimensional biomagnetic information of the (y-z) coordinate can be obtained from the plurality of magnetic sensors 1 held by the second holder portion 16. A first holder face 15a of the first holder portion 15 on which detection faces of the plurality of SQUID sensors 41 are exposed and a second holder face 16a of the second holder portion 16 on which detection faces of the plurality of magnetic sensors 1 are exposed intersect with each other at a substantially right angle in a cross-sectional view (L-shape in the fourth embodiment).

The SQUID sensor 41 requires a temperature control mechanism but capable of a highly sensitive detection of magnetism. Therefore, the biomagnetism measuring device 104 according to the fourth embodiment is capable of obtaining more accurate biomagnetism information than in the case of using only ale magnetic sensor 1, due to using the magnetic sensor 1 (e.g., MR sensor), which is capable of detecting magnetism at normal temperature, together with the SQUID sensor 41.

Biomagnetism Measuring Device According to Fifth Embodiment

The biomagnetism measuring device 105 according to the fifth embodiment is different from the biomagnetism measuring device 104 according to the fourth embodiment in that the magnetic sensor 1 is provided, in addition to the dorsal side and the lateral side of the subject S, in a region between the dorsal side and the lateral side as described later.

Figure 6:
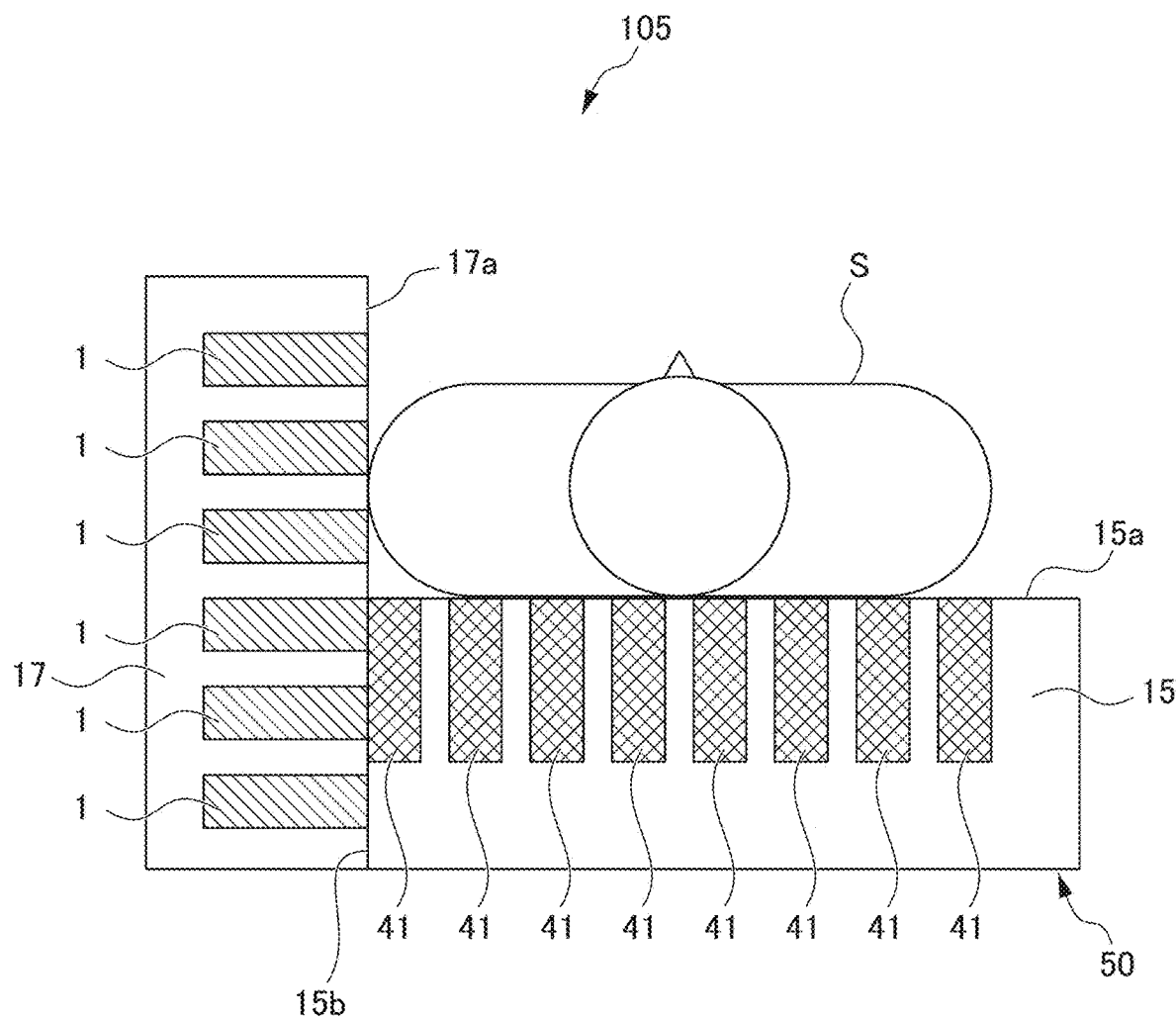
FIG. 6 is a schematic cross-sectional view schematically showing a configuration example of a biomagnetism measuring device according to a fifth embodiment.

FIG. 6 is a schematic cross-sectional view schematically showing a configuration example or a biomagnetism measuring device according to a fifth embodiment. As shown in FIG. 6, the biomagnetism measuring device 105 according to the fifth embodiment includes a holder portion 50 that also serves as a bed. The holder portion 50 is composed of a first holder portion 15 that holds the subject S in a supine position, and a second holder portion 17 arranged on a lateral side of the subject S and on a lateral face 15b side of the first holder portion 15.

In the first holder portion 15, a plurality of SQUID sensors 41 that detects magnetism of a tangential component of the subject S is arranged two-dimensionally in array at coordinate positions in the (x-y) coordinate. As a result, two-dimensional biomagnetic information of the (x-y) coordinate can be obtained from the plurality of SQUID sensors 41 held by the first holder portion 15.

In the second holder portion 17, the plurality of magnetic sensors that detects magnetism of a normal component of the subject S is arranged two-dimensionally in array at coordinate positions in the (y-z) coordinate. As a result, two-dimensional biomagnetic information of the (y-z) coordinate can be obtained from the plurality of magnetic sensors 1 held by the second holder portion 17. A first holder face 15a of the first holder portion 15 on which detection faces of the plurality of SQUID sensors 41 are exposed and a second holder face 17a of the second holder portion 17 on which detection faces of the plurality of magnetic sensors 1 are exposed intersect with each other at substantially right angle in a cross-sectional view (T-shape in the fifth embodiment).

As described above, in the biomagnetism measuring device 105 according to the fifth embodiment, the first holder face 15a and the second holder face 17a intersect with each other in a substantially T-shape in a cross-sectional view, and the magnetic sensor 1 is provided also in the region between the anterior side and the lateral side of the subject S. As a result, the biomagnetism measuring device 105 according to the fifth embodiment is capable of detecting the biomagnetism outside of the detection scopes of the biomagnetism measuring device 104 according to the fourth embodiment, and thus more detailed detection of biomagnetism is possible.

Regarding Holder Portion

In regard to the biomagnetism measuring devices 101 to 105 according to the first to fifth embodiments described above, a method for holding the magnetic sensor 1 (e.g., MR sensor) that can detect magnetism in a thermal environment commensurate with normal temperature is not particularly limited; however, the magnetic sensor 1 is preferably held detachably or movably with respect to the holder portion 10 to 50. Hereinafter, the first holder portion 11 of the holder portion 10 is explained as an example.

Configuration Example 1 of Holder Portion

Figure 7:
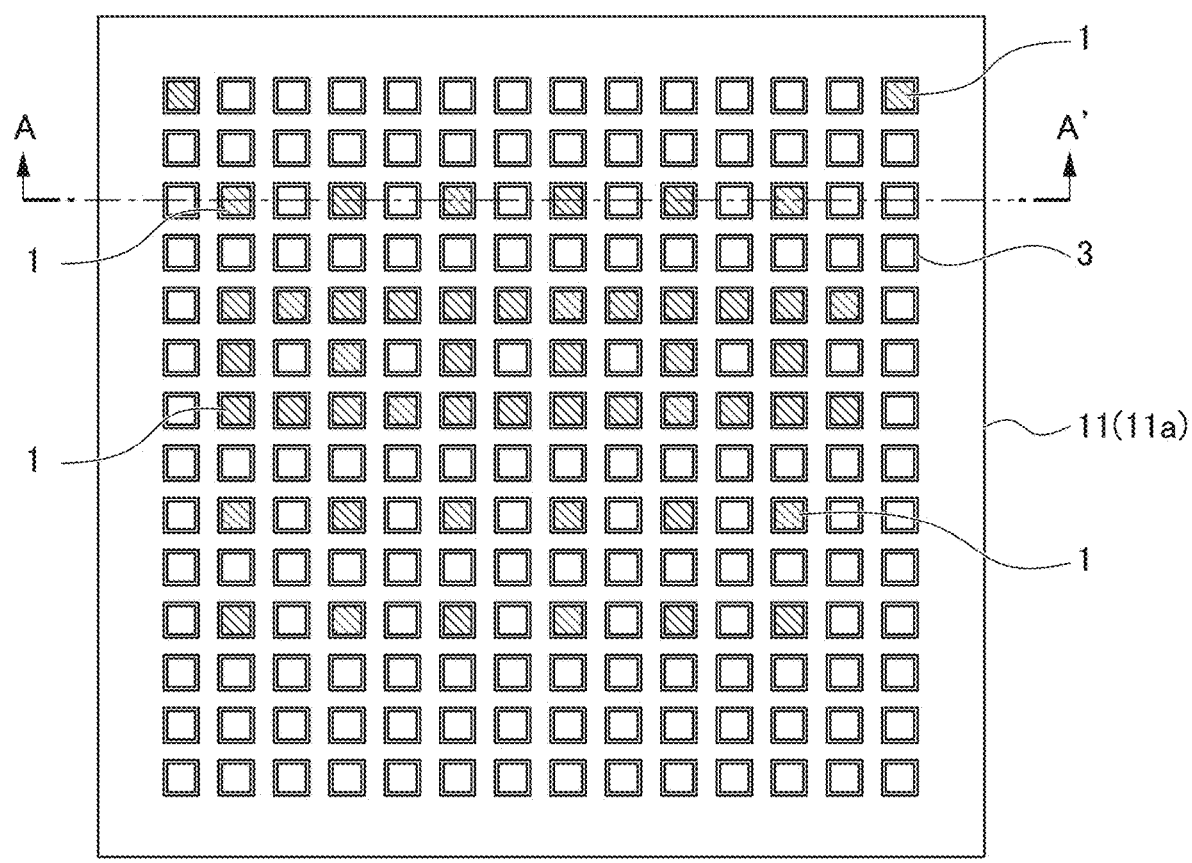
FIG. 7 is a schematic front view schematically showing a configuration example 1 of a holder portion.
Figure 8:
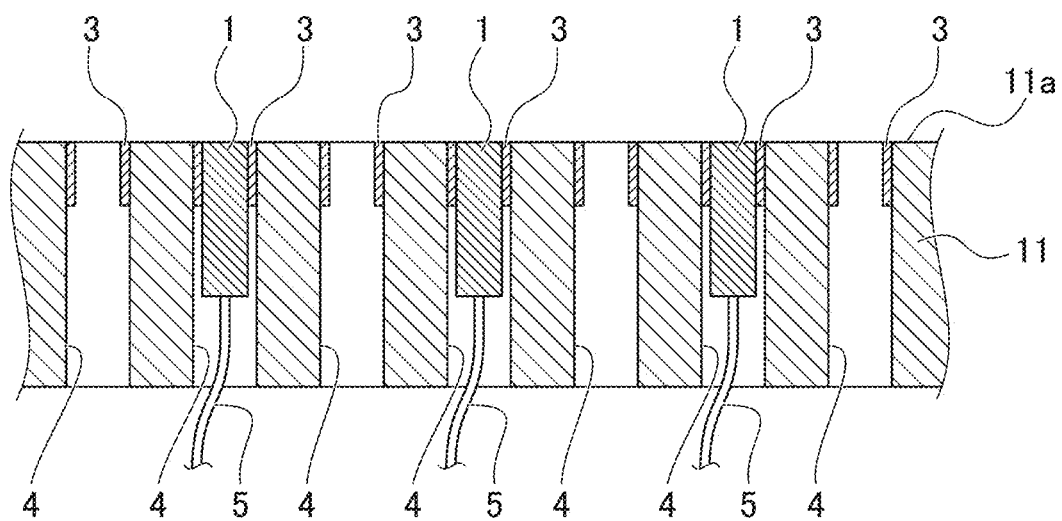
FIG. 8 is a partial enlarged view of a cross section taken along the line A-A' of the holder portion shown in FIG. 7.

FIG. 7 is a schematic front view schematically showing a configuration example 1 of holder portion. FIG. 8 is a partial enlarged view of a cross section taken along the line A-A' of the holder portion shown in FIG. 7. As shown in FIG. 7, for example, on the holder face 11a of the first holder portion 11, substantially square-shaped holding frames 3 that detachably hold. the magnetic sensors 1 are arranged in an array (14×14), and each magnetic sensor 1 is respectively attached to the holding frames 3.

As shown in FIG. 8, the holding frames 3 hold the magnetic sensors 1 such that the detection faces of the magnetic sensors 1 are exposed on the first holder face 11a. More specifically, the magnetic sensor 1 is inserted from a lower side of a holding hole 4 provided on the first holder portion 11 and held by the holding frame 3. A method for holding the magnetic sensor 1 on the holding frame 3 is not particularly limited, and the magnetic sensor 1 may be fixed by a fixture such as a screw formed from a non-magnetic material. Alternatively, the magnetic sensor 1 may be held by fitting, instead of fixing.

Due to holding the magnetic sensor 1 detachably with respect to the holding frame 3 as described above, a desired number of the magnetic sensors 1 may be arranged on desired holding frames 3 as needed, instead of arranging the magnetic sensors 1 on all of the holding frames 3. In other words, the magnetic sensors 1 can be arranged at most appropriate positions in accordance with the physical constitution and sites of the subject S, and the biomagnetic information can be obtained from most appropriate regions. In addition, the magnetic sensors 1 can be arranged densely or sparsely in accordance with a required resolution of a measurement result.

As described above, in light of flexibility of arrangement, the magnetic sensor 1 that can detect magnetism in a thermal environment commensurate with normal temperature is superior to the SQUID sensor 41 that requires fixed arrangement due to the need of a temperature control mechanism. As a result, since no unnecessary magnetic sensor is arranged, signal communication and power supply for the unnecessary magnetic sensor can be eliminated and consequently power saving and cost reduction are made possible.

It is to be noted that the magnetic sensor 1 may or may not have a wiring for signal communication or power supply. However, since the plurality of magnetic sensors 1 is arranged in the biomagnetism measuring device 10 as shown in FIG. 7, the plurality of magnetic sensors 1 preferably has wirings 5 as shown in FIG. 8 in order to avoid crossed wire.

Configuration Example 2 of Holder Portion

Figure 9:
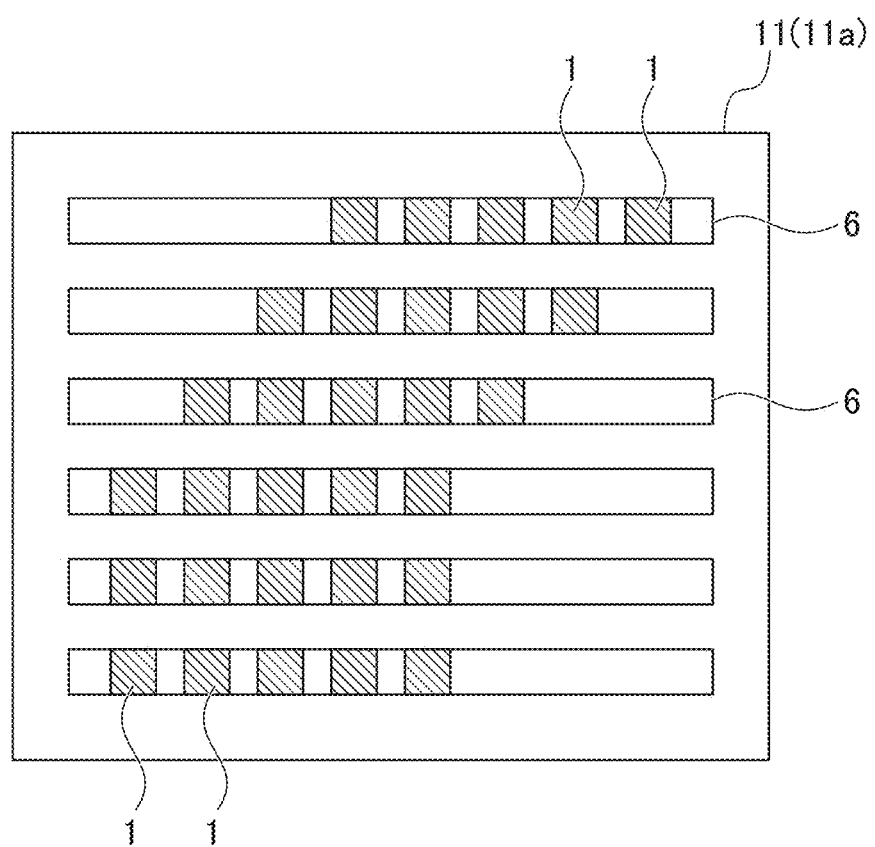
FIG. 9 is a schematic front view schematically showing a configuration example 2 of a holder portion.

FIG. 9 is a schematic view showing a configuration example 2 of the holder portion. As shown in FIG. 9, on the first holder portion 11, a plurality of rails 6 that movably holds the magnetic sensors 1 may be formed in parallel along the longitudinal direction.

(Rail)

The rails 6 movably hold. the magnetic sensors 1 at an arbitrary position. in the longitudinal direction, such that the detection faces of the magnetic sensors 1 are exposed on the first holden face 11a of the first holder portion 11. The magnetic sensor 1 may be either detachable or undetachable with respect to the rail 6.

With the biomagnetism measuring device in which the rails 6 are formed on the first holder portion 11, an operator can easily move the magnetic sensors 1 along the rails 6 and position the magnetic sensors 1 during measurement of the biomagnetism of the subject 5, while checking a measurement result. As described above, similarly to the configuration example 1, due to using the magnetic sensors 1 that can be flexibly arranged, the biomagnetic information can be obtained from most appropriate regions in the configuration example 2.

Configuration Example 3 of Holder Portion

Figure 10:
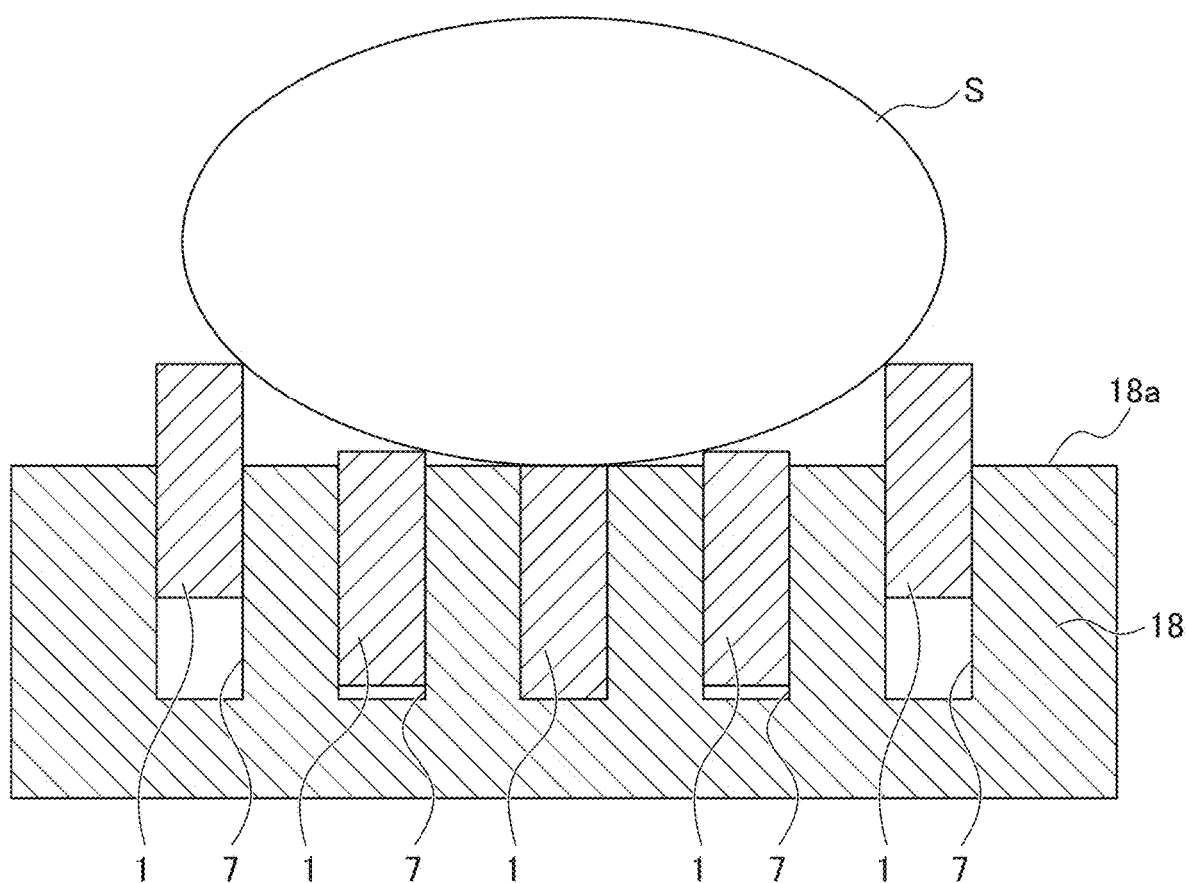
FIG. 10 is a schematic cross-sectional view schematically showing a configuration example 3 of a holder portion.

FIG. 10 is a schematic cross-sectional view showing a configuration example 3 of the holder portion. As shown in FIG. 10, the first holder portion 18 may be provided with a moving mechanism that moves the plurality of magnetic sensors individually inside the holding hole 7, in a contact/separation direction with respect to the subject S. The moving mechanism moves the plurality of magnetic sensors 1 individually in the contact/separation direction with respect to the subject S manually or automatically, to bring the detection faces of the magnetic sensors 1 into close contact with the subject S.

As a result, weak magnetism can be detected with higher sensitivity. The moving mechanism is not particularly limited as long as the magnetic sensors 1 can be moved to predetermined positions and may be exemplified by an air pressure mechanism, a hydraulic pressure mechanism, an elastic material mechanism, a screw mechanism, a gear wheel mechanism and the like. The air pressure mechanism and the hydraulic pressure mechanism are preferred, since these mechanisms use air and oil that do not affect the sensitivity of the magnetic sensor 1.

Jigs such as the holder portions 10, 20, 30, 40, 50 described above (including the holder portions 11 to 18, the holding frame 3, the holding hole 4, the rail t and the like) to which the magnetic sensor 1 is attached are preferably formed from non-magnetic materials such as: a plastic material, e.g., an acrylic resin; a non-ferrous metal, e.g., copper and brass; and wood.

Due to using the non-magnetic material for forming the jigs such as the holder portions 10, 20, 30, 40, 50 to which the magnetic sensor 1 is directly attached, even when these jigs are vibrated by the movement caused by respiration or the like of the subject S, fluctuation of the environmental magnetism can be suppressed and consequently more accurate biomagnetism information can be obtained.

Configuration Example 4 of Holder Portion

The holder portions 10, 20, 30, 40, 50 described above are molded products integrally formed from the non-magnetic material such as the plastic material; however, the holder portion may also be formed from a flexible material.

Figure 11:
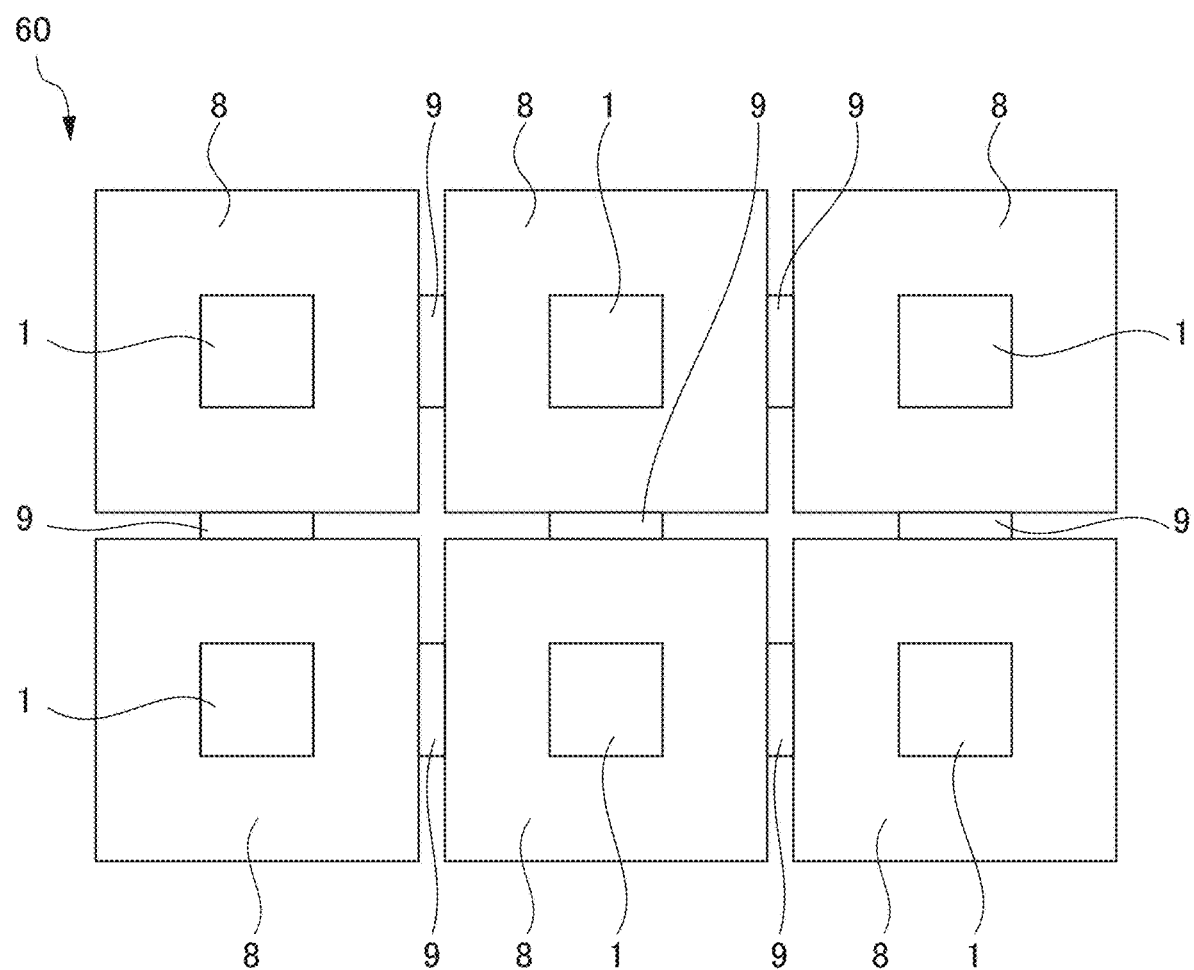
FIG. 11 is a schematic front view schematically showing a configuration example 4 of a holder portion.

FIG. 11 is a schematic front view schematically showing a configuration example 4 of a holder portion. A holder portion 60 shown in FIG. 11 includes a plurality of fixing portions 8 that individually fix the plurality of magnetic sensors 1 and hinges 9 that link the plurality of fixing portions 8. Due to forming the hinges 9 from a flexible material such as rubber, the holder portion 60 allows the magnetic sensors 1 to be arranged to follow the shape of the subject S with irregularities and curvatures, and consequently the detection faces of the magnetic sensors 1 can be in close contact with the body surface of the subject S.

As a result, the biomagnetism measuring device provided with the holder portion 60 is capable of measuring the biomagnetism accurately. It is to be noted that the fixing portion 8 itself may be formed from the flexible material, as long as the fixing portion 8 can fix the magnetic sensors 1.

EXAMPLES

The biomagnetism measuring device 101 according to the first embodiment described above and an X-ray radiography device were provided, to detect biomagnetism of the chest and obtain an X-ray image of the chest. FIG. 12(a) is a diagram showing magnetic field waveform data obtained by the magnetic sensor 1 in the first holder portion 11 arranged on the anterior side of the subject S, and FIGS. 12(b) is a diagram showing magnetic field waveform data obtained by the magnetic sensor 1 in the second holder portion 12 arranged on the lateral side of the subject S.

FIG. 13 is a diagram showing an example of biological information in which magnetocardiogram data built from biological signal data (see FIG. 12) obtained from the biomagnetism measuring device 101 is overlaid on an X-ray image.

As shown in FIGS. 13, diagnosis through overlaying of the biomagnetic information of a magneto cardiogram and the biological information obtained from the X-ray image is possible. In particular, the possibility of diagnosis through overlaying of three-dimensional biomagnetic information and a three-dimensional image obtained by MRI or CT is highly useful.

FIG. 1 is a photograph showing actual measurement of the subject S, using a prototype 103a, which an example of the biomagnetism measuring device 103 (see FIG. 4) according to the third embodiment of the present invention. As described above, in the biomagnetism measuring device 103 according to the third embodiment, the plurality of magnetic sensors 1 is held by the holder portion 30 which is composed of: the first holder portion 11 arranged on the anterior side of the subject S; the second holder portion 13 arranged on the left side of the subject S and the lateral face 11b side of the first holder portion 11; and the third holder portion 14 arranged on the dorsal side of the subject S as shown in FIG. 4; however, since the heart of the subject S is generally on the left side, in the prototype 103a shown in FIG. 14, the second holder portion 13 is arranged to be positioned on the left side of the subject S so as to avoid a defect in the measurement scopes on the anterior side, the distal side, and the left side of the subject S.

It is to be rioted that as a modified configuration. of the prototype 103a, the fourth holder portion (for example the second holder portion 13 shown in FIG. 4 flipped horizontally) may be provdded also on the right side of the subject S to surround. the subject S entirely.

Figure 15:
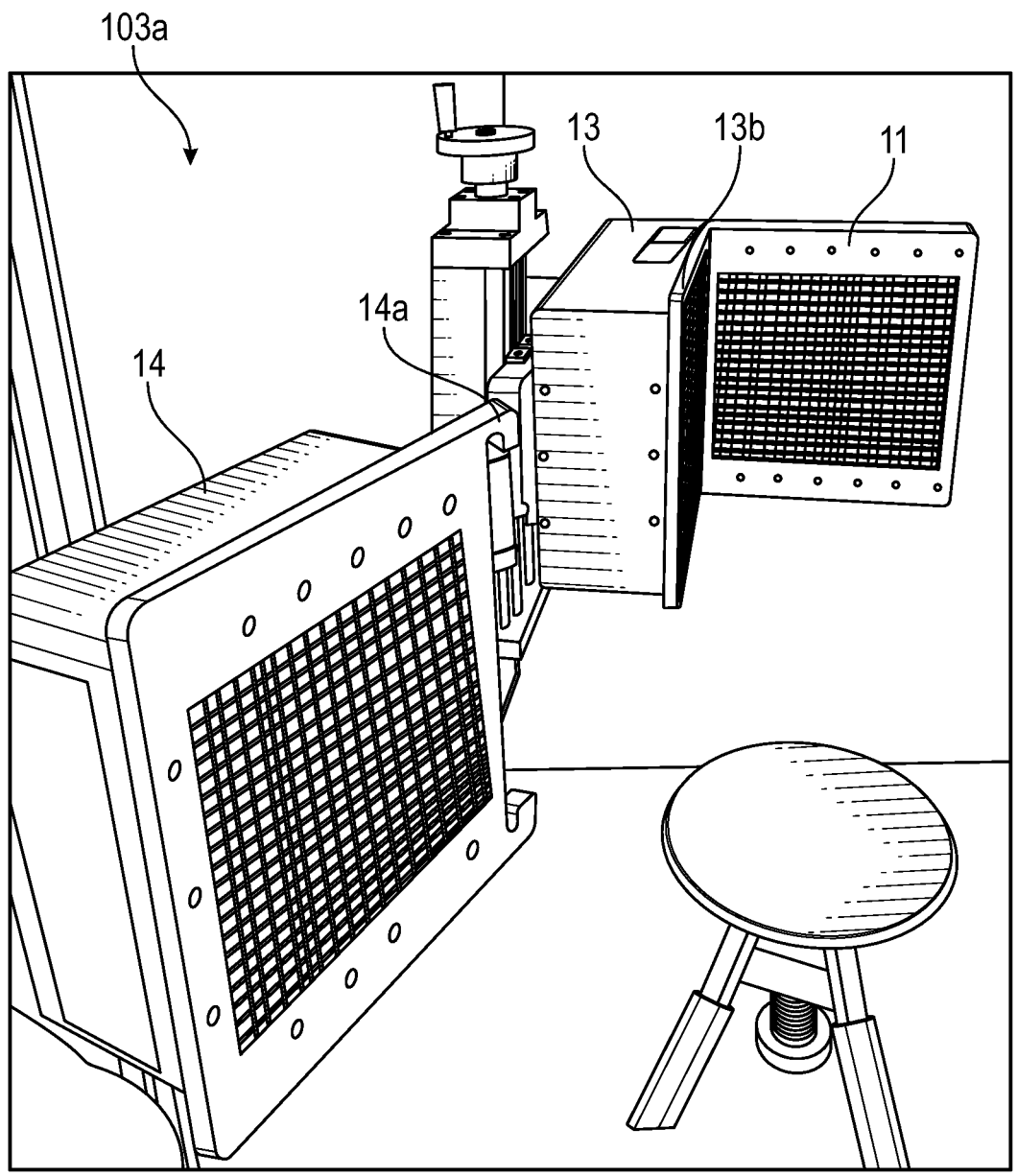
FIG. 15 is a photograph of the prototype employing the third embodiment of the present invention, in which the second holder portion and the third holder portion are separated from each other.

FIG. 15 is a photograph of the prototype 100a in which the second holder portion 13 and the third holder portion 14 arranged on the dorsal side of the subject S are separated from each other. Regarding the prototype 103a, in the holder portion 30 shown in FIG. 4, the first holder portion 11 arranged on the anterior side of the subject S and the second holder portion 13 arranged on the lateral side of the subject S and the lateral face side of the first holder portion 11 are integrally formed in a substantially L-shape in a horizontal cross-sectional view (hereinafter, this member may be also referred to as "L-shaped holder portion"), while the third holder portion 14 arranged on the dorsal side of the subject S is formed in a substantially I-shape in a horizontal cross-sectional view as a separate member from the L-shaped holder portion (hereinafter, this member may be also referred to as "I-shaped holder portion").

Figure 14:
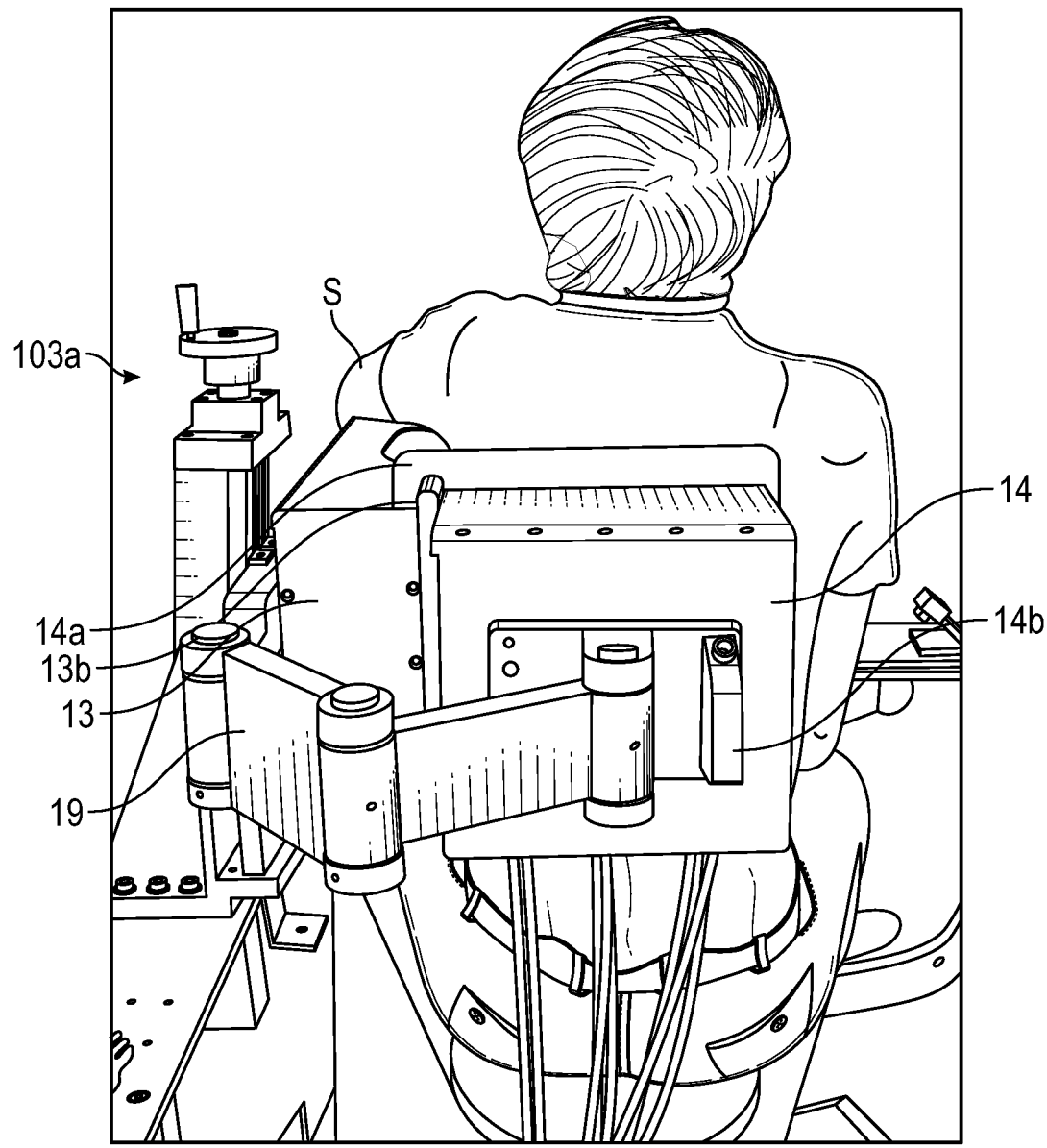
FIG. 14 is a photograph taken from a dorsal side of a subject, showing actual measurement using a prototype employing the third embodiment of the present invention.

As shown in the photographs of FIGS. 14 and 15, the I-shaped holder portion is connected to the second holder portion 13, which is a lateral face of the L-shaped holder portion, with an articulated (trjple-jointed) arm 19 as an example of the open/close mechanism that enables the third holder portion. 14 to open and close; vertical faces of the L-shaped holder portion and the I-shaped holder portion are held at the same height; the I-shaped holder portion is configured to be rotatably separated or engaged horizontally with respect to the second holder portion 13, which is a lateral face of the L-shaped holder portion; and in a state in which the I-shaped holder portion engages with the L-shaped holder portion, the third holder portion 14 of the I-shaped holder portion (constituting a rear face) is parallel to, and movable toward and away from, the first holder portion 11, which is a front face of the L-shaped holder portion.

It is to be noted that a left side of the I-shaped holder portion (a side that engages with the second holder portion 13, which is a lateral face of the L-shaped holder portion) is provided with a pair of flanges 14a that protrudes slightly in a horizontal direction at upper and lower ends, the flanges 14a being configured to movably fit into a guide 13b provided on upper and lower end faces of a lateral face of the L-shaped holder portion.

As a result, in a state in which the guide 13b and the flanges 14a constitute the moving mechanism and the I-shaped holder portion engages with the L-shaped holder portion (see FIG. 14), the third holder portion 14 (i.e., dorsal face) of the I-shaped holder portion is configured to be at a right angle to the second holder portion 13, which is a lateral face of the L-shaped holder portion (in other words, to be parallel to the first holder portion 11, which is a front face of the L-shaped holder portion), while being easily movable toward the front side.

Therefore, in the prototype 103a, in the state in which the L-shaped holder portion and the I-shaped holder portion are separated from each other, the subject S can be easily introduced into and removed from a measurement area of the L-shaped holder portion. Meanwhile, after positioning the subject S at a predetermined measurement position, the I-shaped holder portion can be positioned at a position suitable for the measurement in accordance with the thickness of the chest of the subject S by: engaging the L-shaped holder portion with the I-shaped holder portion; and then moving the third holder portion 14 (i.e., dorsal face) of the I-shaped holder portion toward the first holder portion 11, which is the front face of the L-shaped holder portion, to adjust the position in the horizontal direction.

It is to be noted that the open/close mechanism for separation and engagement between the L-shaped holder portion and. the I-shaped holder portion is not in any way limited to the articulated (triple-jointed) arm 19 shown in the photographs of FIGS. 14 and. 15, and may also be, for example: an articulated arm with two or more joints; a simple track mechanism that extends and contracts only in the horizontal direction; a ball -jointed arm with a high degree of freedom; and the like.

In addition, the guide 13b and the flanges 14a are not in any way limited to the aforementioned moving mechanism, and for example, a mechanism that restricts a movement linearly such as a guide groove and a rail may be provided at an engagement site between the L-shaped holder portion and the I-shaped holder portion.

Alternatively, the third holder portion 14 may be configured to be operable and closable with respect to the first holder portion 11 and movable toward the second holder portion 13. It is to be noted that in the prototype 103*a*, a handle 14*b* is provided on a back face of the I-shaped holder portion as shown in FIG. 14 to facilitate operations of separation and engagement between the L-shaped holder portion and the I-shaped holder portion as described above.

Figure 16:
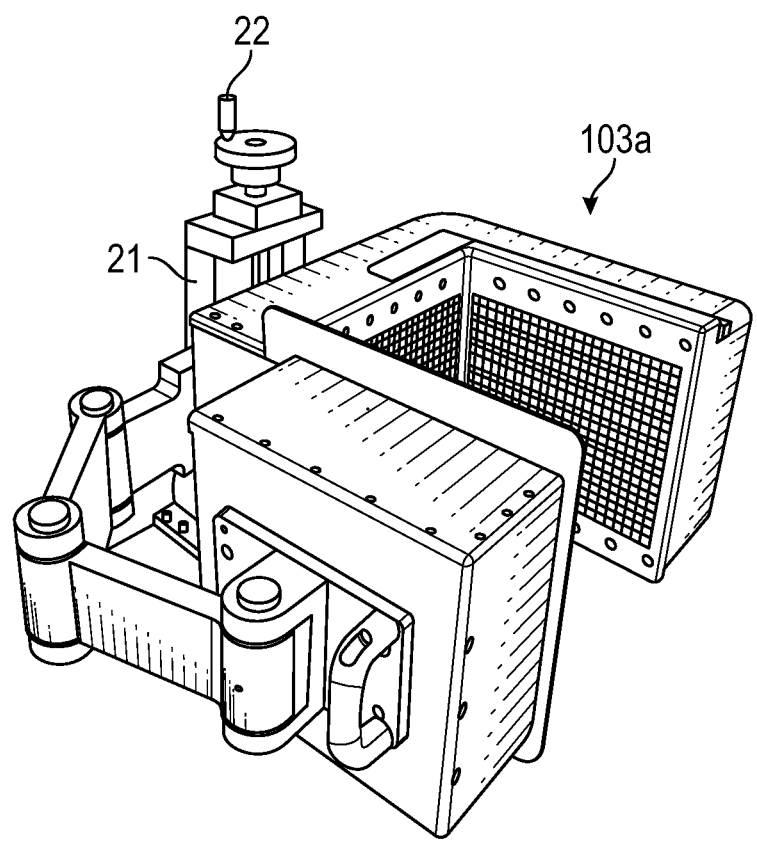
FIG. 16 is a photograph taken in an oblique direction of the prototype employing the third embodiment of the present invention.

FIG. 16 is a photograph showing a connecting mechanism for the L-shaped holder portion in a perpendicular direction of the prototype 103*a* of the biomagnetism measuring device according to the present invention. As shown in FIG. 14, since the prototype 103*a* is for carrying out the measurement of the subject S in a seated position (of course the measurement is also possible in an upright position), the L-shaped holder portion is held via the connecting mechanism vertically transferable with respect to a supporting leg 21 (positioned on the left side of the subject S in FIG. 14) of the prototype 103*a*, such that the L-shaped holder portion can be positioned at an appropriate chest position in accordance with a seated height of the subject S.

The connecting mechanism includes: a first member having a perpendicularly provided rod-like body with an exterior thread, the first member being fixed on the supporting leg 201 side and rotatably held by a rotation handle 22 attached to an upper end of the rod-like body; and a second member having an engagement hole with an internal thread provided in a central part of a semispherical projection, the second member fixed to a lateral face of the L-shaped holder portion via a joint face perpendicular to the projection, in which the rod-like body of the first member is threaded into the engagement hole of the second member, and thus a position in the perpendicular direction is adjusted by rotating the rotation handle 22, to thereby enable displacement of the L-shaped holder portion within a predetermined height range as needed.

It is to be noted that the connecting mechanism for vertically displacing the L-shaped holder portion is not in any way limited to the aforementioned structure and may also be, for example: a structure constituted of a slider and a lock that are displaceable with respect to a vertically arranged rod; a structure obtained by combining a gear drive, a chain drive, etc.; and the like.

Due to including the mechanism allowing position adjustment in the horizontal direction. and the perpendicular direction as described above, the prototype 103 is capable of carrying out measurement in accordance with the physical constitution (in the case of obtaining a magnetocardiogram, heart position), regardless of the physical constitution of the subject S.

EXPLANATION OF REFERENCE NUMERALS

1 Magnetic sensor
2 Operation unit
3 Holding frame
4 Holding hole
5 Wiring
6 Rail
7 Holding hole
8 Fixing portion
9 Hinge
10, 20, 30, 40, 50, 60 Holder portion
11, 15, 18 First holder portion
12, 13, 16, 17 Second holder portion
14 Third holder portion
19 Articulated (triple-jointed) arm
41 SQUID sensor
101, 102, 103, 104, 105 Biomagnetism measuring device

The invention claimed is:

1. A biomagnetism measuring device, comprising:
a plurality of magnetic sensors configured for measuring biomagnetism simultaneously; and
a holder portion,
wherein the plurality of magnetic sensors is held by the holder portion so as to have different measuring directions,
wherein the plurality of magnetic sensors is provided at the holder portion so as to be capable of measuring biomagnetism of multiple sites simultaneously, and
wherein the plurality of magnetic sensors comprises a sensor that detects the biomagnetism in a thermal environment commensurate with normal temperature with no need for cooling, and
wherein the holder portion comprises:
a first holder portion in which the plurality of magnetic sensors is arranged two-dimensionally at positions in a (x-y) coordinate substantially parallel to a body surface of a living organism,
a second holder portion in which the plurality of magnetic sensors is arranged two-dimensionally at positions in a coordinate different from the (x-y) coordinate,
a third holder portion in which the plurality of magnetic sensors is arranged two-dimensionally,
an open/close mechanism that enables the third holder portion to open and close with respect to the first holder portion or the second holder portion, and
a moving mechanism that enables the third holder portion to move toward the first holder portion or the second holder portion.

2. The biomagnetism measuring device according to claim 1, wherein a first holder face of the first holder portion on which the plurality of magnetic sensors is arranged, and a second holder face of the second holder portion on which the plurality of magnetic sensors is arranged are arranged at a substantially right angle in a cross-sectional view.

3. The biomagnetism measuring device according to claim 1, wherein the plurality of magnetic sensors comprises a SQUID sensor.

4. The biomagnetism measuring device according to claim 1, wherein a plurality of holding frames that holds the plurality of magnetic sensors removably or movably is arranged in an array in the holder portion.

5. The biomagnetism measuring device according to claim 1, wherein a plurality of rails that slidably holds the plurality of magnetic sensors is arranged in the holder portion.

6. The biomagnetism measuring device according to claim 1, wherein the holder portion is provided with a moving mechanism that moves the plurality of magnetic sensors individually in a contact/separation direction with respect to the living organism.

7. The biomagnetism measuring device according to claim 1, wherein the holder portion is composed of a non-magnetic material.

8. The biomagnetism measuring device according to claim 1, wherein the holder portion is composed of a flexible material.

9. A method for measuring biomagnetism simultaneously with a plurality of magnetic sensors and a holder portion, the method comprising:

measuring biomagnetism simultaneously by means of the plurality of magnetic sensors, wherein the plurality of magnetic sensors has different measuring directions, wherein the plurality of magnetic sensors is provided so as to be capable of measuring biomagnetism of multiple sites simultaneously, and wherein the plurality of magnetic sensors comprises a sensor that detects the biomagnetism in a thermal environment commensurate with normal temperature with no need for cooling, and wherein the holder portion holds the plurality of magnetic sensors so as to have different measuring directions and the holder portion comprises:

a first holder portion in which the plurality of magnetic sensors is arranged two-dimensionally at positions in a (x-y) coordinate substantially parallel to a body surface of a living organism, a second holder portion in which the plurality of magnetic sensors is arranged two-dimensionally at positions in a coordinate different from the (x-y) coordinate;

a third holder portion in which the plurality of magnetic sensors is arranged two-dimensionally, an open/close mechanism that enables the third holder portion to open and close with respect to the first holder portion or the second holder portion, and a moving mechanism that enables the third holder portion to move toward the first holder portion or the second holder portion.

10. The method according to claim 9, wherein measuring biomagnetism comprising detecting a plurality of directional components for biomagnetism of one site by means of the plurality of magnetic sensors.

* * * * *